(12) United States Patent  
Weiner et al.

(10) Patent No.: US 6,746,448 B2  
(45) Date of Patent: Jun. 8, 2004

(54) OUTRIGGER FOR BONE FIXATOR

(75) Inventors: Lon S. Weiner, Rumson, NJ (US); Thomas Coull, Rancho Palos Verdes, CA (US)

(73) Assignee: Millennium Medical Technologies, Inc., Santa Fe, NM (US)

( * ) Notice: Subject to any disclaimer, the term of this patent is extended or adjusted under 35 U.S.C. 154(b) by 5 days.

(21) Appl. No.: 10/233,897

(22) Filed: Sep. 3, 2002

(65) Prior Publication Data

US 2003/0225406 A1 Dec. 4, 2003

Related U.S. Application Data

(63) Continuation-in-part of application No. 10/160,470, filed on May 30, 2002.

(51) Int. Cl.$^7$ .............................................. A61B 17/56
(52) U.S. Cl. .............................. 606/54; 606/55; 606/59
(58) Field of Search ................................ 606/54, 55, 59

(56) References Cited

U.S. PATENT DOCUMENTS

| | | | | |
|---|---|---|---|---|
| 2,333,033 A | * | 10/1943 | Mraz ............................ | 606/57 |
| 2,393,694 A | | 1/1946 | Kirschner | |
| 4,548,199 A | | 10/1985 | Agee ......................... | 128/92 A |
| 4,611,586 A | | 9/1986 | Agee et al. ................ | 128/92 A |
| 4,628,919 A | | 12/1986 | Clyburn ................. | 128/92 ZK |
| 4,662,365 A | | 5/1987 | Gotzen et al. .......... | 128/92 ZW |
| 4,730,608 A | | 3/1988 | Schlein ..................... | 128/92 Z |
| 4,848,327 A | | 7/1989 | Perdue ....................... | 128/92 R |
| 4,889,111 A | | 12/1989 | Ben-Dov ................. | 128/419 F |
| 4,922,896 A | | 5/1990 | Agee et al. .................... | 606/55 |

(List continued on next page.)

OTHER PUBLICATIONS

Lon Weiner/Millenium Medical Technologies, Wristore Providing Anatomic Reduction, Early Motion, Enhanced Stability, 2 page brochure. It is believed that several copies of this brochure may have been taken by attendees of the 2001 Annual Meeting of the American Academy of Orthopaedic Surgeons, Feb. 28–Mar. 4, 2001, who were not under confidentiality agreement.

*Primary Examiner*—Michael J. Milano  
*Assistant Examiner*—D. Jacob Davis  
(74) *Attorney, Agent, or Firm*—Shewchuk IP Services; Jeffrey D. Shewchuk

(57) ABSTRACT

An external fixator includes a main body and an outrigger for extending over a fractured joint, such as a wrist joint. The main body can be positioned next to a right arm, or flipped over and positioned next to a left arm. The outrigger is attachable to extend either to the left or to the right of the main body, as appropriate. A distal body is removeably connectable to the distal end of the main body, and the distal body can be affixed to bone on the opposite side of the fracture to immobilize the joint where the fracture occurs. The distal body is connected to the main body with an adjustable securement section which provides six degrees of adjustment freedom. The outrigger is attached to the main body through a slide plate in a dual rail configuration which provides two dimensions of adjustment. Fragment pin supports ride in a track of the outrigger, and provide seven degrees of adjustment freedom for directed fixation of fragments at the fracture site. The outrigger is pivotally adjustable relative to the main body, and includes track portions separated by a wrap around angle. The major components of the fixator are molded of plastic. A surgical technique using the fixator includes immobilizing the joint for an initial healing duration and retaining fragment pins in place during a secondary healing duration.

21 Claims, 10 Drawing Sheets

U.S. PATENT DOCUMENTS

| | | |
|---|---|---|
| 5,087,258 A | 2/1992 | Schewior ..................... 606/56 |
| 5,122,140 A | 6/1992 | Asche et al. |
| 5,139,500 A | 8/1992 | Schwartz ..................... 606/96 |
| 5,527,309 A | 6/1996 | Shelton ........................ 606/55 |
| 5,562,661 A | 10/1996 | Yoshimi et al. ............... 606/61 |
| 5,571,103 A | 11/1996 | Bailey .......................... 606/62 |
| 5,620,442 A | 4/1997 | Bailey et al. ................. 606/54 |
| 5,658,283 A | 8/1997 | Huebner ....................... 606/57 |
| 5,662,649 A | 9/1997 | Huebner ....................... 606/57 |
| 5,683,389 A | 11/1997 | Orsak ........................... 606/59 |
| 5,697,934 A | 12/1997 | Huebner ..................... 606/103 |
| 5,810,814 A | 9/1998 | Newson ....................... 606/59 |
| 5,827,283 A | 10/1998 | Groiso et al. ................. 606/57 |
| 5,897,555 A * | 4/1999 | Clyburn et al. ............... 606/54 |
| 5,968,046 A | 10/1999 | Castleman ................... 606/73 |
| 5,989,255 A | 11/1999 | Pepper et al. ................ 606/73 |
| 6,056,748 A * | 5/2000 | Weiner ........................ 606/55 |
| 6,099,529 A | 8/2000 | Gertzman et al. ........... 606/73 |
| 6,123,704 A | 9/2000 | Hajianpour |
| 6,162,225 A | 12/2000 | Gertzman et al. ............ 606/73 |
| 6,171,309 B1 | 1/2001 | Huebner |
| 6,238,417 B1 | 5/2001 | Cole .......................... 606/213 |
| 6,355,037 B1 | 3/2002 | Crosslin et al. |

* cited by examiner

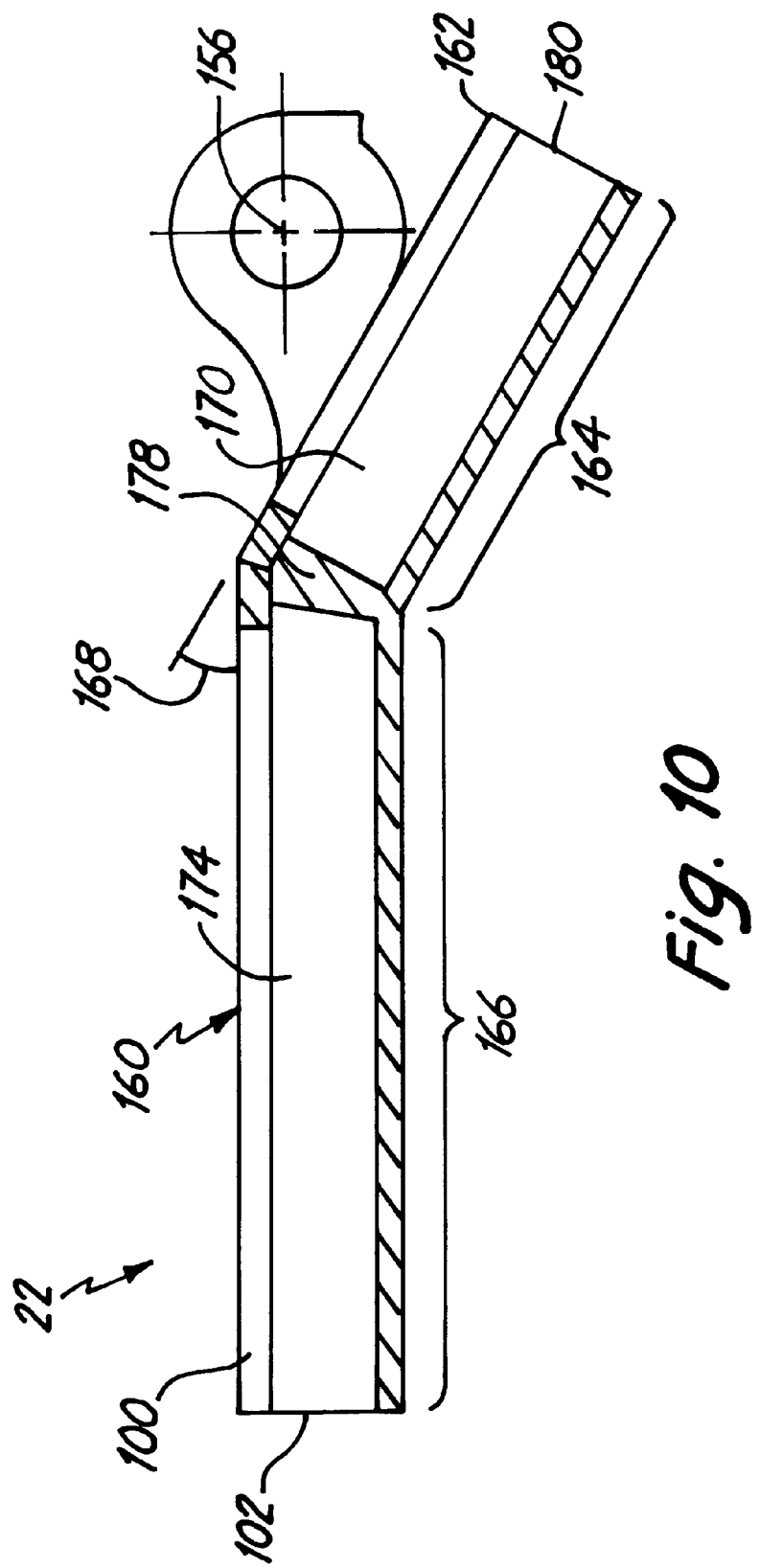

OUTRIGGER FOR BONE FIXATOR

CROSS-REFERENCE TO RELATED APPLICATION(S)

This is a continuation-in-part from application Ser. No. 10/160,470, filed May 30, 2002, entitled FIXATOR WITH OUTRIGGER, incorporated herein by reference.

BACKGROUND OF THE INVENTION

This invention relates to external bone fixators for setting fractures of the human skeleton. In particular, this invention relates to a modular bone fixator assembly for setting fractures of the distal radius and other bones. This invention improves upon the earlier inventions described in U.S. Pat. Nos. 6,056,748 and 6,283,964, both entitled MODULAR FIXATOR ASSEMBLY, which are incorporated herein by reference.

The prior art is replete with external bone fixator devices which are used for setting various bone fractures. Many external bone fixator devices employ transcutaneous pins (e.g., K-wires), stakes, screws or other types of bone fasteners, which are secured in the bone on opposing sides of the fracture. The pins are then secured to an external splint device. The external splint device may use various articulations to adjust its position relative to the bone fasteners. During the fixation surgery, the bone pieces at the fracture may be realigned by the surgeon. The various articulations in the external splint device may assist the surgeon in realigning the bone pieces. Once the external splint device is secured to the bones and the bone pieces are in the desired alignment positions, the articulations in the fixator are locked in place to maintain the bone alignment for a healing duration.

Some of these external bone fixator devices are especially adapted for repairing fractures of the distal radius. This type of fracture often involves a fracture site close to the distal head of the radius. Fractures of the distal head of the radius are commonly referred to as Colles' fractures. Such fractures may be reduced using bone fasteners set on the distal side of the fracture in the metacarpal bone and bone fasteners set on the proximal side of the fracture in the distal half of the radius.

It has been recognized that it is desirable for the wrist to have a certain degree of mobility during the treatment of wrist fractures. However, prior art fixator devices which employ longitudinal traction applied by proximal and distal pins generally do not allow motion at the wrist without crossing the joint during the period of fracture immobilization.

Accordingly, there is a substantial need for improved external fixator devices. The fixator devices need to be strong, rigid and durable, to withstand any forces or inadvertent blows to which the fracture sight is subjected. The fixator devices must be lightweight, so as to movable by the patient without extreme difficulty. The fixator devices should be reasonable in manufacturing cost and difficulty. The fixator devices should facilitate a wide range of surgical techniques, to permit the surgeon to best adapt to the particular fracture and to provide the best mode of healing. In particular, the surgical techniques facilitated by the fixator device should allow the surgeon to quickly reduce the fracture during surgeon while still providing the support needed during the healing duration.

BRIEF SUMMARY OF THE INVENTION

The present invention is a bone fixator using an outrigger, and an outrigger for such a bone fixator. The main body of the fixator is attached to a long bone on one side of a fracture, and holds the outrigger so the outrigger is supported over the fracture site. The outrigger is preferably attachable to extend either to the left or to the right of the main body. The outrigger holds fragment pin supports for adjustments which are not entirely horizontal relative to the bone fixator/long bone plane. The outrigger thus allows the surgeon greater flexibility in moving and fixing bone fragment pins as desired relative to the fracture.

BRIEF DESCRIPTION OF THE DRAWINGS

FIG. 10 is a cross-sectional side view of the outrigger of FIGS. 8 and 9, taken along line 10—10.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

Figure 2:
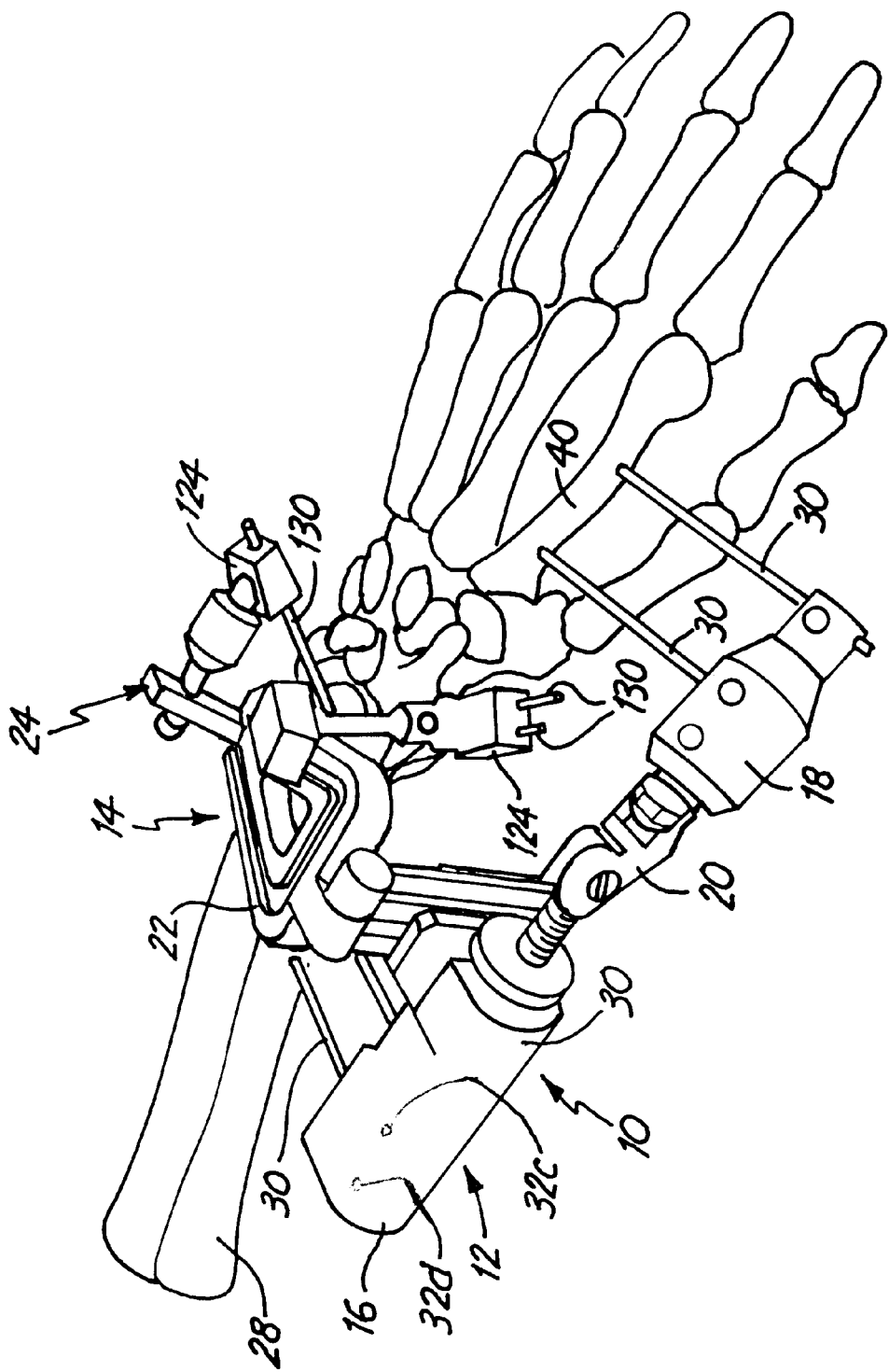
FIG. 2 is a perspective view showing the fixator of FIG. 1, reconfigured for fixation of the left wrist and shown attached relative to a left wrist skeleton, and also depicted using the alternative outrigger of FIG. 7.

A preferred fixator assembly 10 according to the present invention includes, as primary components, a splint or distractor device 12, and an outrigger section 14. The distractor device 12 preferably includes a proximal pin clamp member or main body 16 and a distal pin clamp member or distal body 18. The distal body 18 is attached to the main body 16 by a securable adjustment segment 20. The outrigger section 14 includes an outrigger 22 shown holding two fragment pin supports 24. The outrigger section 14 is attached to the distractor device 12 with an outrigger attachment 26. The fixator assembly 10 is generally used for repairing fractures of bones, especially fractures of the distal radius 28 as shown in FIG. 2.

The main body 16 is adapted to be fixed to a long bone, which for the preferred embodiment is the distal third of the radius 28. The main body 16 is thus somewhat elongated to reflect the elongated extent of the distal third of the radius 28. The main body 16 includes structure for securing it to proximal bone fasteners 30. In the preferred embodiment, bone fasteners 30 extend through apertures or clamp openings 32 in the main body 16. The clamp openings 32 extend through the main body 16 transversely relative to the longitudinal axis 34 of the main body 16. The preferred bone fasteners 30 are 3 mm bone pins or "K-wires", but many other types of bone fasteners (such as relatively long, thin bone screws, etc.) could equivalently be used. The bone pins 30 described throughout this application may be affixed into the bone (reamed, driven, compression or distraction, etc.) as taught in U.S. Pat. Nos. 6,056,748 and 6,283,964.

During the fixation surgery, the bone pins 30 are preferably inserted through the clamp openings 32 and surgically staked into the distal radius 28. The bone fasteners 30 may for instance be directed through the main body portion 16 prior to surgical insertion into the radius 28. Alternatively, the bone pins 30 may be staked into the distal radius 28 and the main body 16 placed over the staked bone pins 30, but threading the bone pins 30 through the clamp openings 32 prior to/during affixation to the bone aids in aligning the bone pins 30 relative to the radius 28. Threading the bone pins 30 through the clamp openings 32 prior to/during affixation to the bone also aids in spacing and aligning the bone pins 30 relative to the main body 16.

Once the bone pins 30 are set in the distal radius 28 and advanced as desired relative to the clamp openings 32 in the main body 16, the bone pins 30 are secured in place relative to the main body 16. For instance, the main body 16 may be positioned relative to the bone pins 30 and the radius 28 such that the main body 16 rests on the soft tissue and skin of the forearm. Alternatively, the surgeon may position the main body 16 spaced a short distance from the tissue of the forearm. The preferred structure to secure the bone pins 30 relative to the main body 16 is with set screws 36 (shown without detail). The set screws 36 are threaded into set screw holes 38 which intersect the clamp openings 32. Tightening of the set screws 36 will secure the main body 16 relative to the surgically staked bone pins 30.

Figure 1:
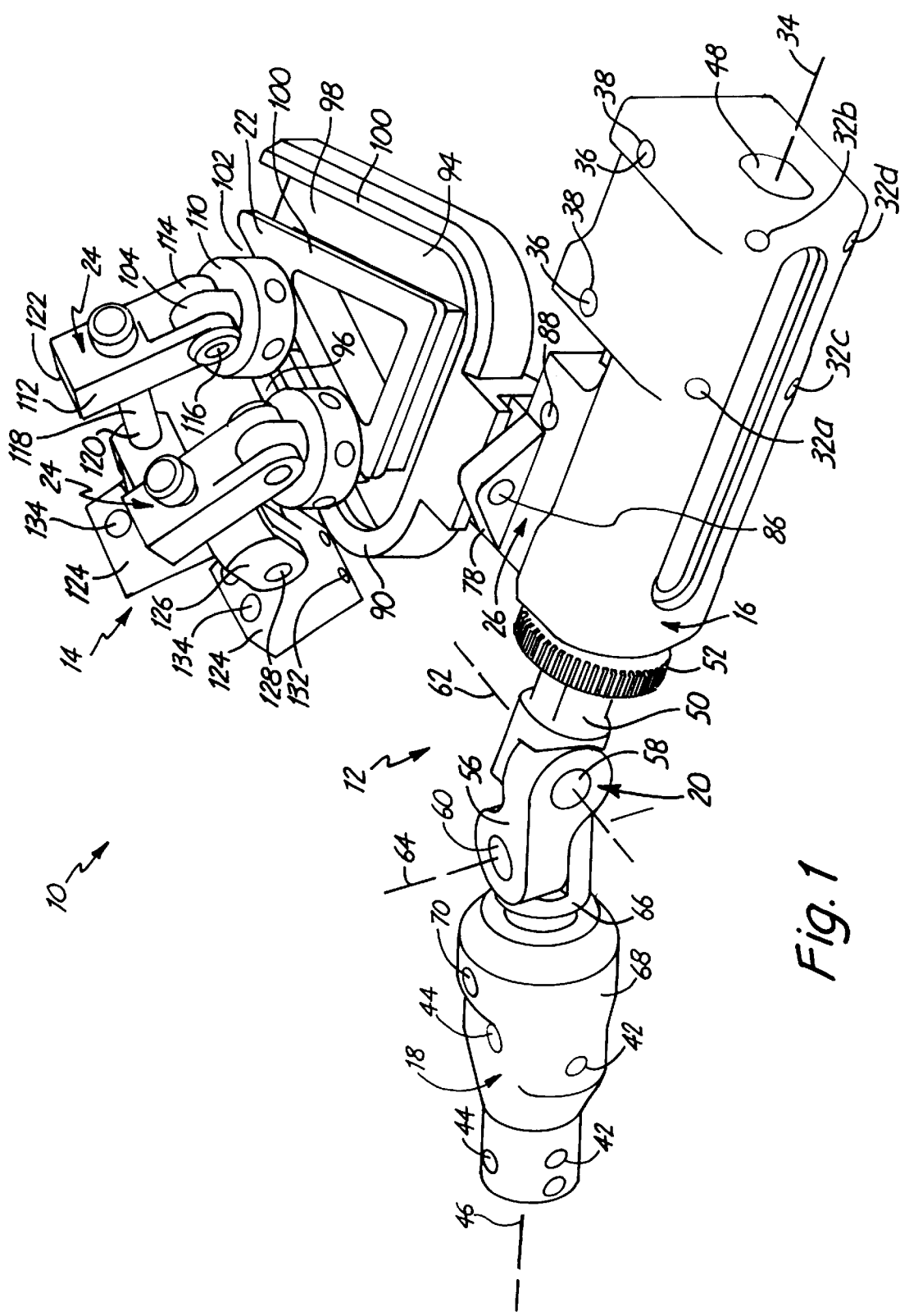
FIG. 1 is a perspective view of a preferred embodiment of the present invention configured for fixation of the right wrist, shown for simplicity without bone pins and without detail on the heads of the set screws.

The main body 16 can be positioned in either of at least two orientations relative to the long bone (radius 28), and the mechanism for securing the main body 16 to the long bone (radius 28) preferably accommodates such multiple orientations. For instance, the main body portion 16 of the preferred embodiment includes two pairs of clamp openings (32a and 32b, 32c and 32d). One pair 32a, 32b of the clamp openings 32 extend on one side of the longitudinal axis 34 of the main body 16 (i.e., above the longitudinal axis 34 as shown in FIG. 1), and the opposing pair 32c, 32d of the clamp openings 32 extend on the other side of the longitudinal axis 34 (i.e., below the longitudinal axis 34 as shown in FIG. 1). When positioned for use on the right arm as shown in FIG. 1, the upper set 32a, 32b of clamp openings 32 will preferably be used, with the lower set 32c, 32d of clamp openings 32 left vacant. Use of the upper set 32a, 32b of clamp openings 32 places the main body 16 at an elevation relative to the radius 28 which best positions the main body 16 relative to intended subsequent placement of the distal body 18 and the outrigger 22, and also minimizes the moments that the weight of the fixator 10 will place on the radius 28 during normal use.

The lower set 32c, 32d of clamp openings 32 provide some flexibility should the surgeon desire to use the fixator 10 at a higher elevation relative to the radius 28. However, the primary importance of the lower set 32c, 32d of clamp openings 32 is to provide flexibility so the main body 16 can be equivalently be used on either right or left arms. As shown in FIG. 2, the main body 16 can be flipped for use with the left arm at the same relative height, simply by utilizing the bone pins 30 through the second (now upper) set 32c, 32d of clamp openings 32. The preferred embodiment thus includes four clamp openings 32a, 32b, 32c, 32d, with only the upper two (which can be either set depending upon left or right orientation) being primarily intended for use. The clamp openings 32a, 32b are longitudinally spaced about 1½ inches apart, about two inches from the distal end of the main body 16. This spacing is adequate to support the main body 16 on the radius 28, while not coming too close to the typical Colles' fracture site in the radial head. If desired, additional bone pin clamp openings may be placed in the main body 16, to give the surgeon additional flexibility in placement of the bone pins 30. Similarly, if desired the main body may be made longer, giving the surgeon potential attachment sites into the middle or proximal thirds of the radius 28. In any orientation, the main body 16 is intended to be affixed such that its longitudinal axis 34 extends roughly parallel to the longitudinal axis of the radius 28.

The distal pin clamp body 18 of the fixator 10 is used for attachment on the opposite side of the fracture, and serves as a joint fixation body in conjunction with the main body 16 to fix the position of the joint. In the preferred embodiment for use with a Colles' fracture, the distal body 18 is to be secured to a metacarpal and particularly the second metacarpal 40, thereby setting the wrist and preventing the wrist from flexing during the healing of the Colles' fracture.

Similar to clamp openings 32 of the main body 16, the distal body 18 also includes transverse clamp openings 42 for transcutaneous bone pins 30 or other bone fasteners. With the distal body 18 of the preferred embodiment, the distal transcutaneous bone pins 30 are surgically set into the second metacarpal 40. A preferred placement location positions the first metacarpal pin 30 about 5 mm distal to the second metacarpal joint. The distal body 18 is secured relative to the bone pins 30 with set screws 44 (shown in FIGS. 1 and 3 without detail), and thereby positioned such that its longitudinal axis 46 extends roughly parallel to the longitudinal axis of the metacarpal 40. A spacing between the distal clamp openings 42/distal bone pins 30 of about one inch is appropriate for attachment into the metacarpal 40. Because the distal body portion 18 does not support the mass and the concomitant potential moment of the outrigger 22, a single set of clamp openings 42 are provided which intersect the longitudinal axis 46 of the distal body 18. If desired however, additional distal clamp openings may be provided to give the surgeon additional options in securing the distal body 18 relative to the second bone 40.

The distal body 18 is attached to the main body 16 by the secureable adjustment segment 20. If desired, the distal body 18 can be attached with a universal joint allowing pivotal movement of the distal body 18 to the main body 16, similar to that taught in U.S. Pat. Nos. 6,056,748 and 6,283,964. For some applications, the distal body 18 may be attached with a simple pin-type hinge, or may even be permanently secured relative to the main body 16. However, the preferred secureable adjustment segment 20 includes four degrees of adjustable freedom, each separately securable.

As a first degree of freedom, the main body 16 defines a bore 48 which extends axially therein, and an extension rod 50 is received in the bore 48. The extension rod 50 allows the fixator 10 to be lengthened or shortened as appropriate for the particular size of patient being treated. Any of several mechanisms can be used so the surgeon can control the extension rod 50. In the preferred embodiment, the extension rod 50 is externally threaded. A thumb screw 52 is attached on the main body 16 such that it is free to rotate. The thumb screw 52 has internal threads which mate with the external threads of the extension rod 50, such that rotation of the thumb screw 52 advances or retracts the extension rod 50. The longitudinal position of the extension rod 50 is lockable via a rod set screw 54 (shown without detail in FIG. 3).

Second and third degrees of adjustment freedom are provided by a yoke section 56, which permits angular adjustment of the distal body 18 relative to the main body 16. The yoke section 56 is bolted with a horizontal bolt 58 (shown in FIG. 1 without detail) to a distal end of the extension rod 50 and with a vertical bolt 60 (shown in FIG. 1 without detail) to a proximal end of the distal body 18. Each end of the yoke section 56 includes a peak/valley radially-toothed profile which mates with similarly toothed profiles on the extension rod 50 and distal body 18. Loosening of the horizontal bolt 58 permits pivoting of the yoke section 56 about a generally horizontal axis 62 defined by the horizontal bolt 58. Loosening of the vertical bolt 60 permits pivoting of the distal body 18 about a generally vertical axis 64 defined by the vertical bolt 60. Tightening of the horizontal bolt 58 and the vertical bolt 60 secures the distal body 18 at the desired horizontal and vertical angles relative to the longitudinal axis 34 of the main body 16. The horizontal and vertical bolts 58, 60 preferably include hexagonal recesses to permit tightening and loosening with an allen wrench. Alternatively, a hexagonal head or a head for a flat or Phillips screwdriver, or even thumbscrews may be used.

As a fourth degree of adjustment freedom, the distal body 18 is provided as a central rod 66 (shown in FIG. 6 and in dashed lines in FIG. 5) with a rotatable outer clamp member 68. A set screw 70 (shown without detail in FIG. 1) is provided in a mating threaded hole in the rotatable outer clamp member 68. With the set screw 70 loosened, the outer clamp member 68 freely rotates relative to the central rod 66. With the set screw 70 tightened, the outer body 68 is secured to the central rod 66. Further, the set screw 70 can be fully loosened to permit the outer clamp member 68 to be readily removed from the secureable adjustment segment 20.

If desired, additional degrees of adjustment freedom may be provided by the securable adjustment segment 20. For instance, the extension rod 50 and/or bore 48 may be shaped and configured to permit rotation between the main body 16 and the extension rod 50. The rod set screw 54 could then function to secure the position of the extension rod 50 relative to the main body 16 both longitudinally and rotationally. As another example, the rotatable outer clamp member 68 may be slidable on the central rod 66 to permit extension of the distal body 18. The set screw 70 would then function to secure the position of the outer clamp member 68 relative to the distal body 18 both longitudinally and rotationally.

One purpose of the adjustment freedom provided by the secureable adjustment segment 20 is to maximize the options available to the surgeon with respect to placement of the bone pins 30 into the second bone (i.e., in the preferred embodiment, into the second metacarpal 40). In particular, the fixator 10 can be secured both to the radius 28 and to the second metacarpal 40 with the secureable adjustment segment 20 fully loose, allowing the surgeon ease of motion to stake the bone pins 30 through the fixator 10 and into the bone. A second purpose of the adjustment freedom provided by the secureable adjustment segment 20 is to maximize the options available to the surgeon with respect to the healing orientation of the bones at the fracture site. After the fixator 10 is secured both to the radius 28 and to the second metacarpal 40, the surgeon can then manipulate the wrist joint to the desired bone healing position, including the appropriate reduction, distraction, palmer flexion and ulnar deviation. The surgeon can perform the desired manipulation of the wrist joint either by applying pressure directly on the wrist joint itself or with the aid of the fixator 10 by properly moving the main body 16 and distal body 18 to thereby manipulate the bones. Once the wrist joint is in the desired bone healing position, the bolts 58, 60 and the set screws 44, 54, 70 are fully tightened so the wrist position is rigidly held by the fixator 10.

While traditional fixation can be performed with the distractor device 12, the present invention particularly contemplates use for direct fragment fixation. Direct fragment fixation is performed with the outrigger section 14. The outrigger 22 is preferably removably attached to the main body 16. The outrigger 22 may be attached to the main body 16 during surgery, that is, after fixation of the main body 16 to the radius 28 and the distal body 18 to the second metacarpal 40, and after securement of the securable adjustment segment 20. By attaching the outrigger 22 to the main body 16 after such fixation and securement, the surgeon has better access to the wrist joint during the fixation and securement steps. Alternatively, the outrigger 22 may be attached to the main body 16 prior to surgery or prior to the fixation and adjustment steps. As an alternative but less flexible embodiment, the outrigger 22 may be permanently secured to the main body 16.

Figure 5:
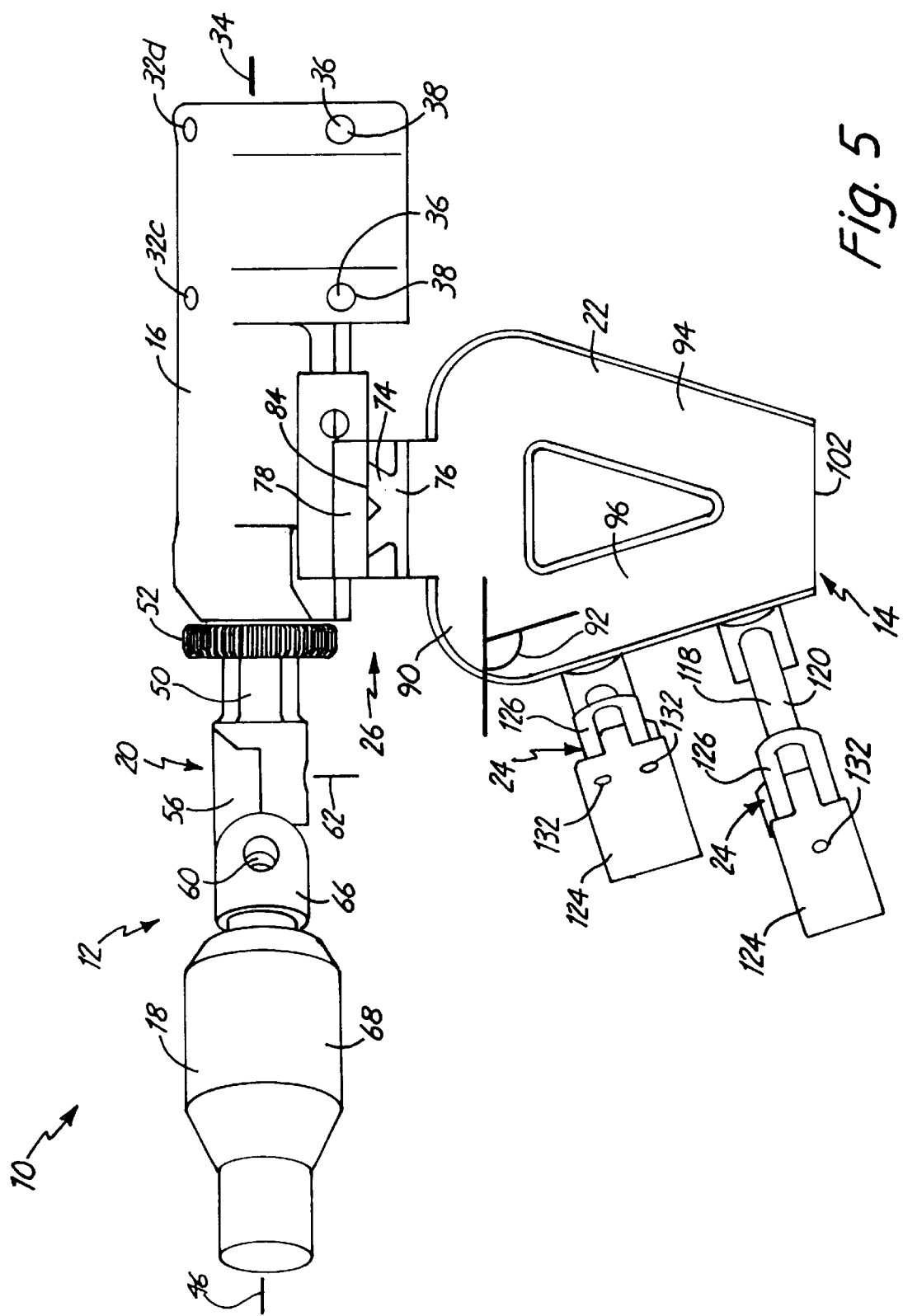
FIG. 5 is a bottom (from the proximal) view of the fixator of FIG. 1, shown with bolts removed from their respective holes 58, 60 and with a simplified distal end 18.
Figure 6:
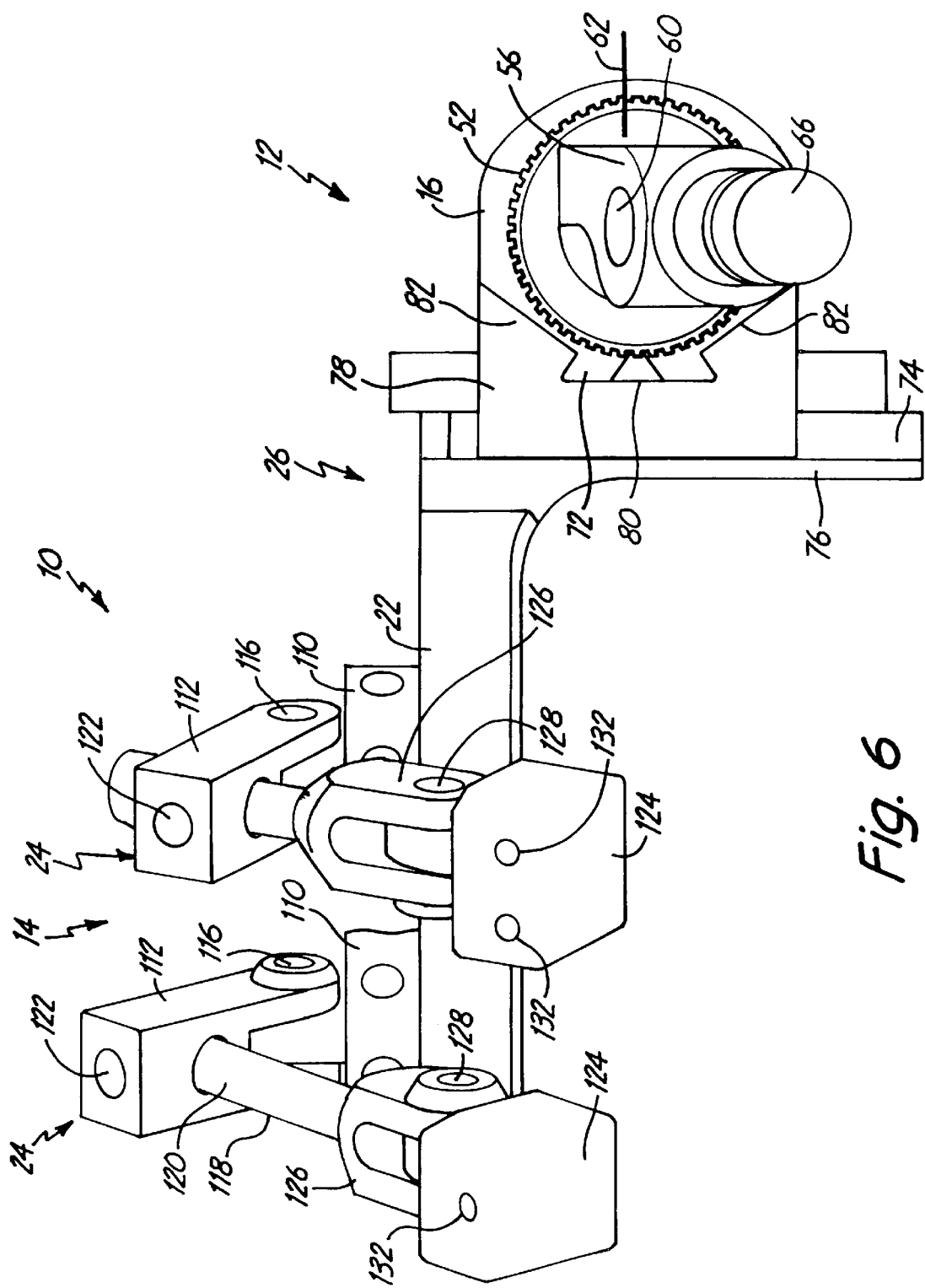
FIG. 6 is an end (from the distal) view of the fixator of FIG. 1, shown without the rotatable outer clamp member of the distal body.

If desired, the outrigger 22 may be attached to the main body 16 by a mounting member with thumb gear as taught in U.S. Pat. Nos. 6,056,748 and 6,283,964. In the preferred embodiment, however, the outrigger section 14 is attached to the distractor device 12 with a dual sliderail configuration provided by the outrigger attachment 26. As best shown in FIGS. 5 and 6, the outrigger attachment 26 includes a rail 72 disposed on the main body 16, a rail 74 disposed on a flange 76 of the outrigger 22, and a slide plate 78 which operates in conjunction with the two rails 72, 74. As best shown in FIG. 6, the main body rail 72 is provided on a side of the main body 16 toward the fracture site. While the main body rail 72 could extend in any direction, the main body rail 72 in the preferred embodiment extends longitudinally, parallel to the longitudinal axis 34 of the main body 16. This orientation provides the main body rail 72 while adding the minimal amount of mass and bulk to the main body 16. The main body rail 72 mates in sliding engagement with a first slide recess 80 provided on the slide plate 78.

On opposing sides of the main body rail 72, the slide plate 78 abuts rail plate portions 82 of the main body 16 to provide for maximum vertical stability of the outrigger 22. The rail plate portions 82 could be co-planar or in parallel planes, but the preferred rail plate portions 82 on the main body 16 extend at angles to each other to better match a generally cylindrical outer profile of the main body 16.

As best shown in FIG. 5, a second slide recess 84 is provided on the opposite side of the slide plate 78, facing away from the main body 16. The second slide recess 84 extends at an angle and preferably perpendicular relative to the first slide recess 80. The outrigger rail 74 on the flange 76 of the outrigger 22 mates in sliding engagement with the second slide recess 84. On opposing sides of the outrigger rail 74, the slide plate 78 abuts the outrigger flange 76 to provide for maximum horizontal stability of the outrigger 22. The abutment sides of the preferred outrigger flange 76 are co-planar.

For both the outrigger rail 74 and the main body rail 72, the preferred shape of the rail is a dovetail having a head and a neck which is narrower in cross-section than the head. This shape securely limits movement of the sliding engagements other than in the slide direction, while still being relatively easy to mold. The preferred length of the slide rails 72, 74 is about 1½ inches, which has been found sufficient to adequately support the outrigger 22 relative to the main body 16 while still permitting ½ inch or so of adjustability without significant loss of rigidity.

In the preferred outrigger attachment 26, two distinct modes of separability are available. The main body rail 72 is exposed at its distal end, and the mating recess 80 of the slide plate 78 is exposed at its proximal end. This allows removal of the slide plate 78 from the main body 16 simply by sliding the slide plate 78 fully in the distal direction. Attachment of the slide plate 78 to the main body 16 is performed oppositely, by properly positioning the slide plate 78 relative to the main body 16 and sliding the slide plate 78 in the proximal direction.

The outrigger rail 74 is exposed at its anterior end, and the mating recess 84 of the slide plate 78 is exposed at both its anterior and its dorsal end. This allows removal of the outrigger 22 from the slide plate 78 simply by pulling upward on the outrigger 22. Because the mating recess 84 of the slide plate 78 is exposed at both ends, the outrigger 22 can be removed in the upward direction regardless of the orientation of the slide plate 78, that is, regardless of whether the main body 16 is positioned for a right arm with the outrigger 22 extending to the right (FIG. 1) or flipped over and positioned for a left arm with the outrigger 22 extending to the left (FIG. 2). Attachment of the slide plate 78 to the main body 16 is performed oppositely, by properly positioning the outrigger 22 relative to the slide plate 78 and pushing downward.

The two modes of separability give the surgeon flexibility in determining when and how to attach the outrigger 22 to the main body 16. The slide plate 78 may be attached to the main body 16 before or after securing the main body 16 to the radius 28. Similarly, the outrigger 22 may be attached to the slide plate 78 before or after other portions of the surgical procedure. The sliding motion also permits infinite fine position adjustability of the outrigger 22. In particular, the outrigger 22 should be placed with 1 cm of clearance over the radial articular surface.

Figure 3:
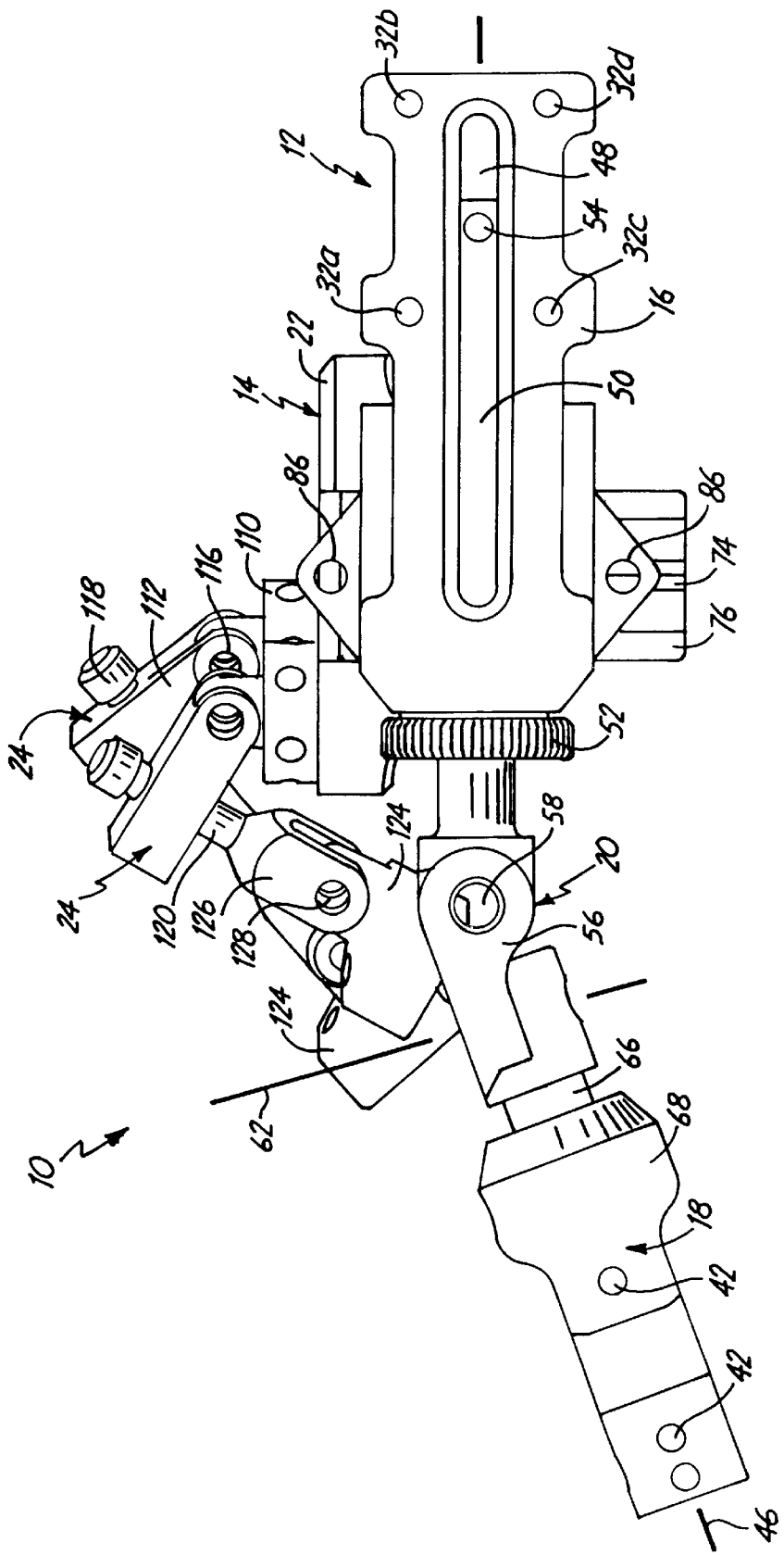
FIG. 3 is an elevational view of the fixator of FIG. 1, shown with set screws and bolts removed from their respective holes 58, 60, 86, 116 and 128.

Releasable securements are provided for securing the rails 72, 74 relative to the their respective slide recesses 80, 84. A first set screw in set screw hole 86, best shown in FIGS. 1 and 3, is used to set the vertical height of the outrigger 22 relative to the main body 16. A second set screw in mating set screw hole 88, best shown in FIGS. 1 and 5, is used to fix the longitudinal extent of the main body 16 relative to the outrigger triangle 22. Both of these set screws 86, 88 are easily accessible to the surgeon from the top of the fixator assembly 10. A similar set of set screw holes 86, 88 is positioned on the other side of the main body 16, for use when the outrigger 22 is attached to extend to the left over a left arm (FIG. 2).

If desired, the outrigger can be provided as the I-shaped metallic member shaped as taught in U.S. Pat. Nos. 6,056, 748 and 6,283,964. In the preferred embodiment, however, the outrigger 22 is provided with a rigid triangular shape, best shown in FIGS. 5, 8 and 9. The outrigger 22 with this triangular shape projects generally perpendicular to the outrigger flange 76. The triangular shape is inherently very strong, particularly against deflection from any cantilevered bending stresses placed on the outrigger 22. The triangular shape generally conforms to the anatomical configuration of the distal radius 28. In particular, the coronal anatomy of the radius 28 proceeds from the radial styloid backward at an angle of about 102° to 110° (depending upon the anatomy of the particular patient) relative to the longitudinal axis of the radius 28. The triangular shape of the outrigger 22 proceeds back from a distal corner 90 at an angle 92 which should be between about 95° and 118° relative to the longitudinal axis 34 of the main body 16. The angle 92 of the outrigger 22 preferably proceeds at 98° to 115° relative to the longitudinal axis 34 of the main body 16, more preferably at 102° to 110° (i.e., coinciding with the 12–20° angle of the distal head of the radius 28), with a most preferred value being 110°. This angle 92 not only conforms to the anatomical configuration of the distal radius 28, but also provides an outrigger shape which is inherently strong and well supports the cantilevered stresses placed on it by the fragment fixation pin supports 24. That is, a proximal leg 94 cooperates with a distal leg 96 to stabilize and strengthen the outrigger 22. Rigidity is enhanced because the proximal leg 94 and the distal leg 96 are well separated at their attachment to the outrigger flange 76. The preferred outrigger triangle 22 extends from the flange 76 for nearly three inches, but is still sufficiently long because the triangle 22 is over two inches wide including a nearly one inch attachment to the flange 76.

The preferred triangular shape only has the distal leg 96 which extends backward at an angle of 110°, with the proximal leg 94 extending forward at an angle of 70°. Only the distal leg 96 is expected to be used for any particular fixation. Of course, when the fixator 10 is used on the opposite arm (from right to left), the direction in which the outrigger 22 faces is reversed (from right to left), and the opposite leg 94 of the triangular shape becomes the more distal of the two legs 94, 96.

The dual slide rail configuration gives two degrees of freedom in placing the outrigger 22 with respect to the main body 16. If desired, an additional degree of freedom may be provided as depicted in the alternative outrigger 150 of FIG. 7 and the alternative outrigger 160 of FIGS. 8–10. The embodiment of FIG. 7 and the embodiment of FIGS. 8–10 both include a securable hinge 152. The preferred attachment between the securable hinge 152 and the flange 76 is shown only in FIG. 7, but workers skilled in the art will appreciate that such disclosure applies equally to the embodiment of FIGS. 8–10. The preferred attachment between the securable hinge 152 and the flange 76 includes a tightening bolt 154 provided between the base of the triangle 22 and the flange 76. This securable hinge 152 allows pivoting of the triangle 22 relative to the main body 16, about a horizontal axis 156 parallel to the longitudinal axis 34 of the main body 16. In the preferred embodiment, the securable hinge 152 allows a range of pivoting from at least +30° to at least −10° relative to horizontal. Thus, a (generally horizontal) reference plane for treatment of the fracture can be defined as a plane containing the longitudinal axis of the long bone and the longitudinal axis 34 of the main body 16. The securable hinge 152 pivotably attaches the outrigger 150, 160 to the main body 16 such that pivotal adjustment of the outrigger 150, 160 changes an angle of the bone fastener support movement direction relative to the reference plane.

Figure 7:
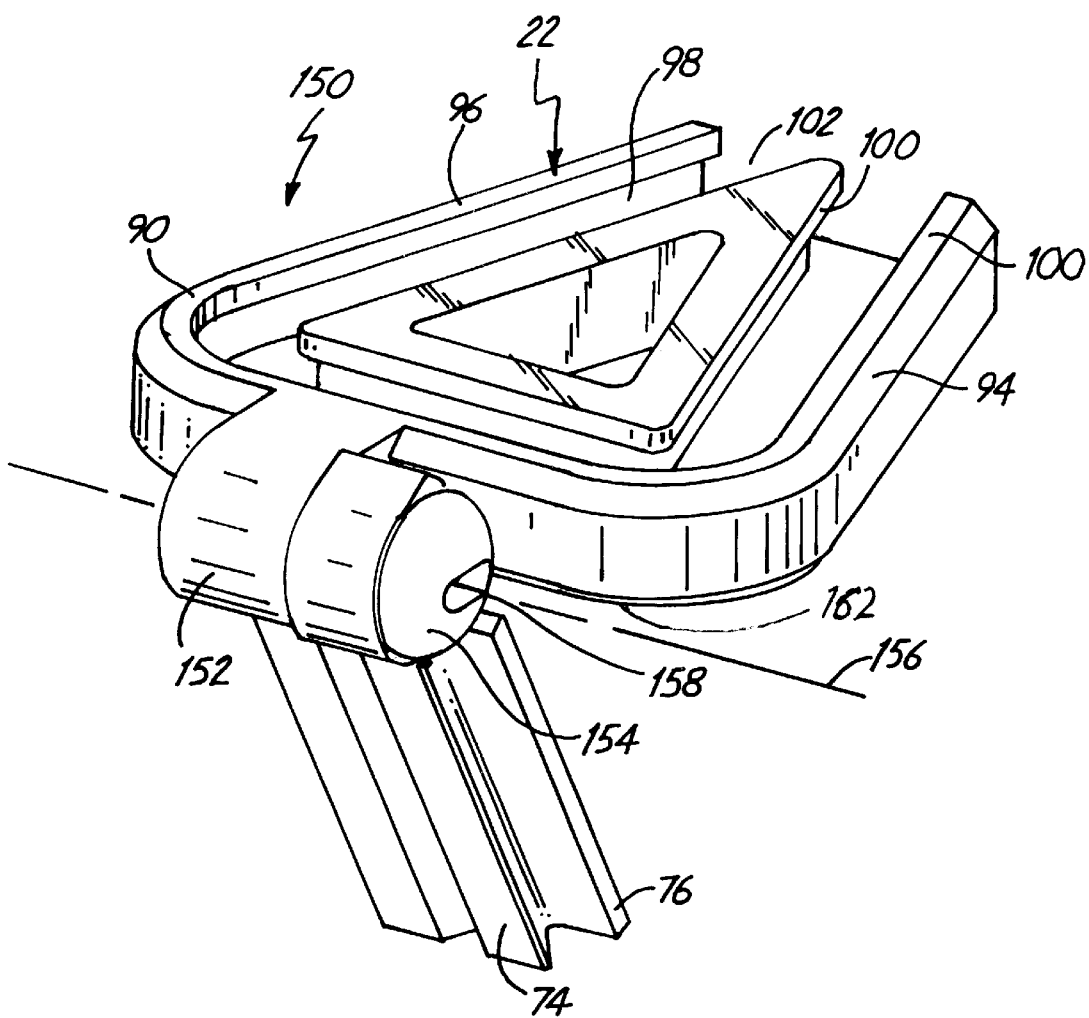
FIG. 7 is a perspective view showing an alternative outrigger assembly.

The securable hinge 152 pivotably attaches the outrigger 150, 160 to the main body 16 such that the bone fastener support movement direction can be selected at a greater range of positive angles than negative angles, for two reasons. First, as best shown in FIGS. 7 and 10, the outrigger 150, 160 has a lower corner 162 which, depending upon the configuration of the flange 76 and the slide plate 78, may be the point of first interference for the outrigger 150, 160 to prevent the outrigger 150, 160 from pivoting to further negative angles. If further negative angles are desired, material may be removed from the lower corner 162 and/or the flange 76 or slide plate 78 (FIG. 7) to allow further rotation. Second, positive angles are generally more desirable than negative angles because positive angles tend to position the outrigger pivoting axis 156 closer to the fracture site. Having the outrigger pivoting axis 156 close to the fracture site generally minimizes obstruction and makes the surgical procedure easier. Having the outrigger pivoting axis 156 close to the fracture site minimizes the distance that the fixator 10 extends from the arm, minimizing the likelihood that the fixator will prove unwieldy or awkward to the patient while wearing the fixator. Having the outrigger pivoting axis 156 close to the fracture site also generally minimizes the moments placed upon the main body 16 by forces on the fragment pins 130. That is, angling the outrigger 150, 160 at positive angles relative to the (horizontal) reference plane creates more of a wrap-around relationship between the fixator 10 and the fractured bone, which facilitates both surgical placement and recovery.

As shown in FIG. 7, the tightening bolt 154 has a head with a slot 158 for a flat head screwdriver. By tightening of the tightening bolt 154, the rigid securability of the outrigger triangle 22 relative to the main body 16 can be maintained at the position ultimately selected by the surgeon.

Figure 4:
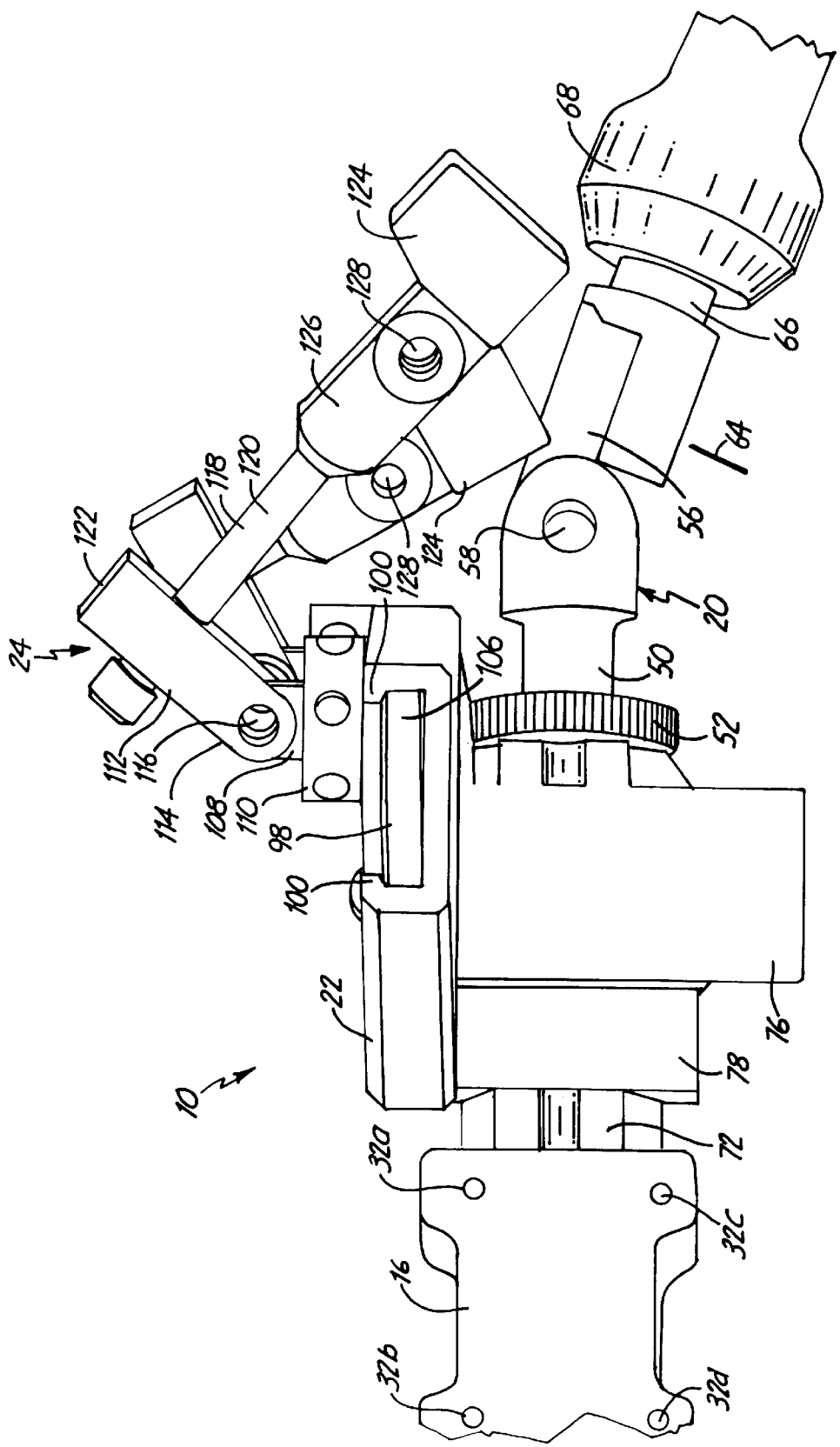
FIG. 4 is an opposite elevational view of the fixator of FIG. 1, shown with bolts removed from their respective holes 58, 116 and 128.

The legs 94, 96 of the outrigger 22 define tracks having a sliding recess 98. As best shown in FIGS. 1 and 4, the sliding recess 98 includes opposing lip sections 100, which assist in supporting and holding the fragment pin supports 24. The track configuration of the outrigger 22 is inherently strong and rigid while still being relatively lightweight.

The preferred sliding recess 98 has an open end 102. This open end 102 permits removal of the fragment pin supports 24 from the track 98. Thus, the surgeon can determine how many fragment pin supports 24 should be lined up in the track 98 for any particular surgery. If desired, the first fragment pin support 24 can be secured in place before the second (or third, etc.) fragment pin support 24 is placed into the track 98.

Figure 8:
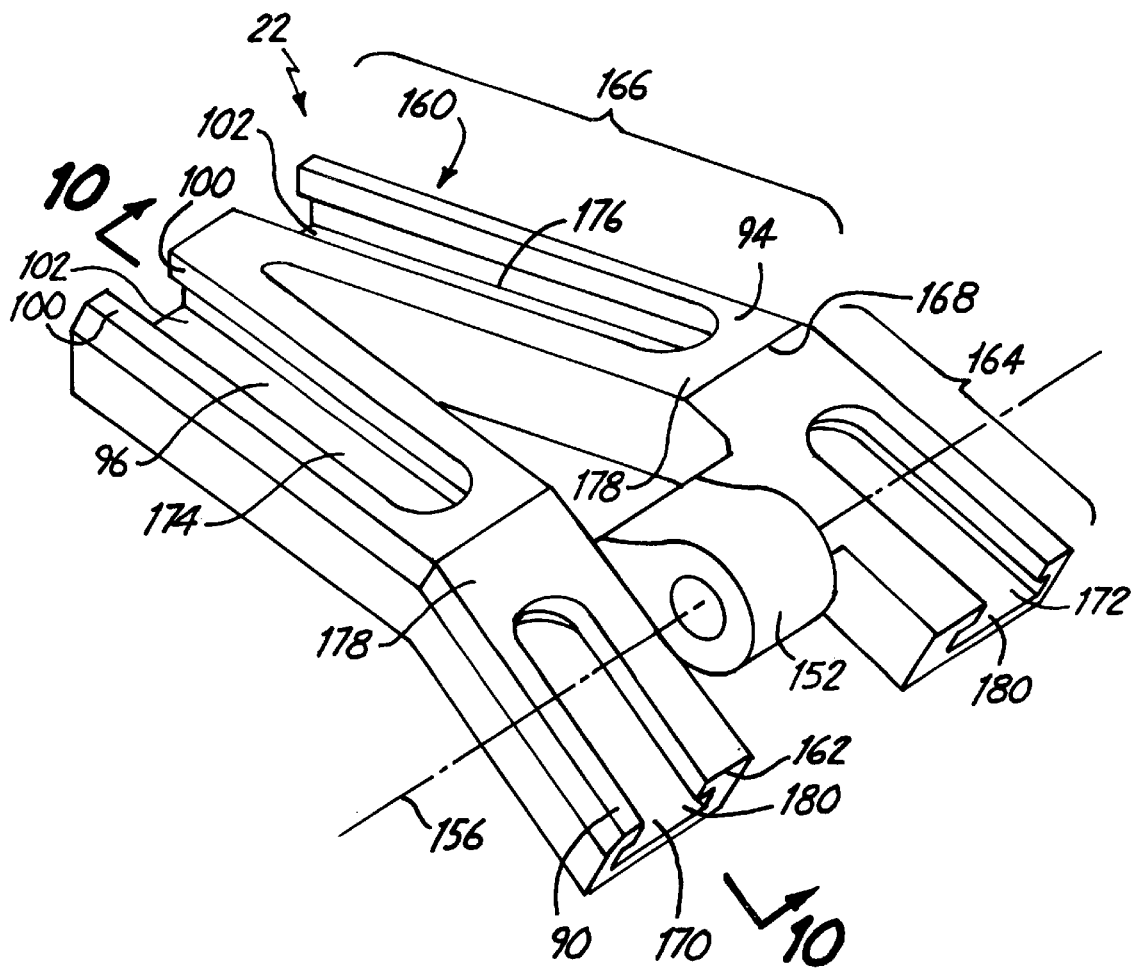
FIG. 8 is a perspective view showing a second alternative outrigger.
Figure 9:
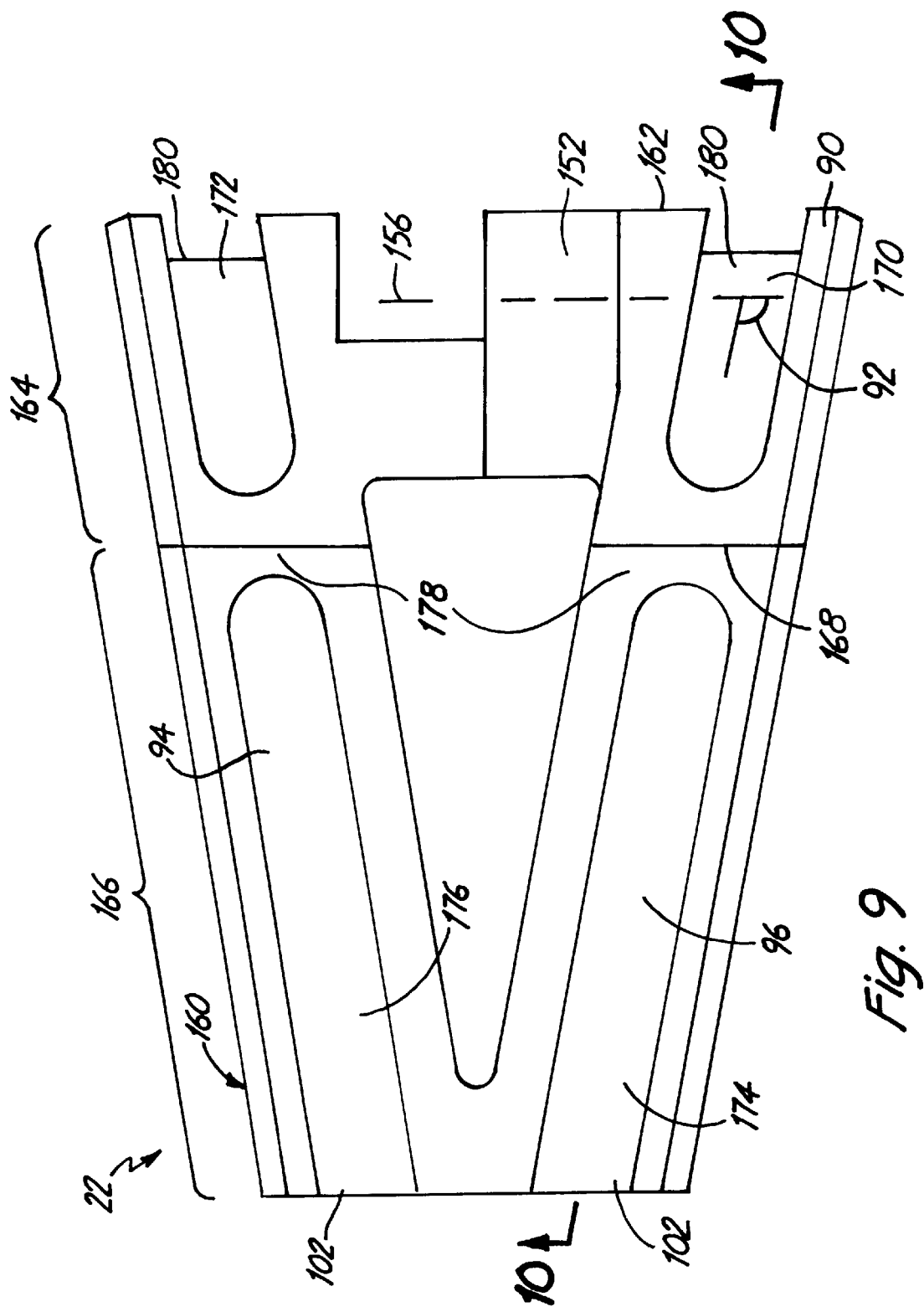
FIG. 9 is a top view of the outrigger of FIG. 8.

A most preferred outrigger 160 of the present invention is shown in FIGS. 8–10. Outrigger 160 is formed to have a proximal section 164 extending in a first plane, and a distal section 166 extending in a second plane. A wrap-around angle 168 between the proximal section 164 and the distal section 166 can be designed as desired to optimize the desired movement directions for the fragment pin supports 24. The proximal section 164 includes a track portion 170 for right hand use and a track portion 172 for left hand use. The distal section 166 includes a track portion 174 for right hand use and a track portion 176 for left hand use. Both track portion 170 and 174 for right hand use extend at the angle 92 relative to the axis 34 of the main body (and the axis of the radius). However, because track portion 170 extends in proximal section 164 and track portion 172 extends in distal section 166, track portions 170 and 174 are not co-linear, but instead somewhat wrap around the fracture site of the distal radius. With two track portions 170 and 174, the desired wrap around angle 168 is less than 50°, and more preferably greater than about 15° and less than about 45°, and most preferably about 35°. Other values could be designed for the wrap around angle 168, and particularly shallower values for wrap around angle 168, including shallower wrap around angle values for constructions using more than two track portions 170, 174. Track portions 172, 176 for left hand use similarly benefit from the wrap around angle 168.

The wrap around angle 168 allows the surgeon two defined bone fastener support movement directions, each of which is generally parallel to a tangent of the distal radius taken at the nearest point. With the wrap around angle 168, two or more fragment pins 130 can be readily directed into the fracture site from different locations (for instance, at roughly 11 o'clock and 12 o'clock orientations about the radial axis), and readily aligned so each fragment pin 130 is generally as perpendicular as possible to the bone surface at the point of contact. Regardless of the angle of the adjustable hinge 152 selected by the surgeon, at least one of the track portions 170, 174 is angled relative to a horizontal reference plane, such that the sliding movement of the fragment pin support 24 therein adjustably changes elevation of that fragment pin support 24. Thus, the wrap-around angle 168 allows the bone fastener support movement directions to correspond even more closely with the coronal anatomy of the radius 28. That is, a (generally horizontal) reference plane for treatment of the fracture can be defined as a plane containing the longitudinal axis of the long bone and the longitudinal axis 34 of the main body 16. Because of the wrap-around angle 168, the movement direction of at least one of the fragment pin supports 24 is sloped at an angle relative to the reference plane.

The proximal track portion 170 for right hand use and the distal track portion 174 for right hand use are separated by a strengthening web 178. Similarly, the proximal track portion 172 for left hand use and the distal track portion 176 for left hand use are separated by a strengthening web 178. The strengthening webs 178 coincide with the wrap around angle 168 between the proximal portion and the distal portion of the outrigger 160. The strengthening webs 178 help the outrigger 160 to withstand forces and moments while maintaining sufficient rigidity at the wrap around angle 168, a location which otherwise would inherently increase the amount of bending deflection which can be induced in the fixator 10.

The most preferred outrigger 160 has open ends or track openings 180 located proximally on the outrigger 160 toward the main body 16. The track openings 180 allows the surgeon to introduce and/or remove the fragment pin support 24 from the proximal track portions 170, 174 without moving any fragment pin support 24 which is already in place in the distal track portions 172, 176. Thus, each proximal track portion 170, 174 has its own track opening 180, while each distal track portion 172, 176 has its own open end 102.

By having each fragment pin support 24 having a separate opening 102, 180, the surgeon has additional flexibility in deciding when to add second (and third, etc.) fragment pin supports 24 and their associated fragment pins 130, and in deciding when to remove those fragment pin supports 24 and their associated fragment pins 130, without necessarily adjusting or moving fragment pin supports 24 and their associated fragment pins 130 which the surgeon desires to keep in place. For instance, after a temporary placement or after an initial healing duration, the surgeon could add or remove a proximal fragment pin support 24 and its associated fragment pin 130, without moving without adjusting or moving either the outrigger 160 or a distal fragment pin support 24.

The outrigger 22, 150 or 160 securely and adjustably locates the fragment pin supports 24 as shown in FIGS. 1–6. If desired, the fragment pin supports may be similar to those described in U.S. Pat. Nos. 6,056,748 and 6,283,964. However, the preferred fragment pin supports 24 shown herein are molded plastic structures. The preferred fragment pin supports 24 provide seven degrees of adjustment freedom in locating the fragment pins 130 into the distal radius 28.

As a first degree of adjustment freedom and best shown in FIGS. 1 and 4, each fragment pin support 24 includes a knob bolt 104 which slidably rides within the track 98. The surgeon can select the desired location of each knob bolt 104 in the track 98. The knob bolt 104 has a head 106 on a threaded shaft section 108. The head 106 mates with the track 98 including the opposing lip sections 100, to hold the shaft section 108 rigidly upright with respect to the outrigger 22. A tightening nut 110 is used on the shaft 108 to releaseably secure the knob bolt 104 at the selected location in the track 98.

If desired, the head 106 of the knob bolt 104 can be elongated or otherwise have flats which mate with the walls of the track 98, to more securely hold the knob bolt 104 relative to the outrigger 22. However, as a second degree of adjustment freedom, the head 106 of the knob bolt 104 is cylindrical without any flats. This allows the surgeon, while the tightening nut is loose, to rotate the knob bolt 104 about the generally vertical axis defined by shaft 108 of the knob bolt 104, changing the direction in which the fragment pin support 24 extends from the track 98.

A third degree of adjustment freedom is provided by a pivot arm 112. The pivot arm 112 includes a fork 114 which mates over the extending end of the knob bolt 104. The tines of the fork 114 receive a pivot arm bolt 116, with one of the tines threadingly engaging threads of the pivot arm bolt 116. Similar to the yoke section 56, the tines of the fork 114 may have a peak/valley radially-toothed profile which mates with similarly toothed profiles on the projecting end of the knob bolt 104. Alternatively, the frictional engagement between flat surfaces of the pivot rod fork 114 and the knob bolt 104 may be sufficient to secure the angular position of the knob bolt 104. Loosening of the pivot arm bolt 116 permits pivoting of the pivot arm 112 about a generally horizontal axis defined by the pivot arm bolt 116. Tightening of the pivot arm bolt 116 secures the pivot arm 112 to the knob bolt 104 at a desired angle. The preferred pivot arm 112 has a length of less than an inch, just enough to substantially avoid interference between the fragment pin support 24 and the outrigger triangle 22.

Fourth and fifth degrees of adjustment freedom are provided by a connecting rod 118. The preferred connecting rod 118 has a cylindrical shaft 120 which slides in a cylindrical hole in the extended end of the pivot arm 112. The cylindrical shaft 120 allows the connecting rod 118 to be slid upwards and downwards relative to the pivot arm 112, and also allows the connecting rod 118 to be pivoted about the axis defined by the connecting rod shaft 120. A set screw 122 (shown without detail in FIG. 6) is threaded into a threaded set screw hole in the exposed end face of the pivot arm 112. The set screw 122 can be tightened to secure the connecting rod 118 in its desired amount of extension and a desired rotational position relative to the pivot arm 112. In the preferred embodiment with two fragment pin supports 24, one of the connecting rods 118 may be longer than the other, such as having lengths of about 1½ inches and 2 inches. The shaft 120 of the connecting rod 118 (which in the preferred embodiment form the thinnest link of the fixator 10) must be sufficiently thick to rigidly support the pin holder 124, such as a diameter of the connecting rod shaft 120 of about ⅕ inch.

A sixth degree of adjustment freedom in the fragment pin support 24 is provided by the pin holder 124. The pin holder 124 is received between the tines of a fork 126 on the end of the connecting rod 118. The tines of the connecting rod fork 126 receive a connecting rod bolt 128, with one of the tines threadingly engaging the connecting rod bolt 128. Similar to the yoke section 56 and the pivot arm fork 114, the tines of the connecting rod fork 126 may be flat or may have a peak/valley radially-toothed profile which mates with a similarly toothed profile on the pin holder 124. Loosening of the connecting rod bolt 128 permits pivoting of the pin holder 124 about a generally horizontal axis defined by the connecting rod bolt 128. Tightening of the connecting rod bolt 128 secures the pin holder 124 at the desired angular position.

The seventh degree of adjustment freedom is provided by the connection between the fragment pins 130 and the pin holder 124. The pin holder 124 includes at least one through hole 132 for receiving the fragment pin 130. A threaded set screw hole intersects the fragment pin through hole 132, and a threaded set screw 134 (shown in FIG. 1 without detail) is tightenable to secure the fragment pin 130 relative to the pin holder 124.

Each of the set screws 36, 44, 54, 70, 86, 88, 122, 134, the pivot arm bolt 116 and the connecting rod bolt 128, all shown in the drawings without detail, preferably include hexagonal recesses to permit tightening and loosening with an allen wrench. Alternatively, a hexagonal head or a head for a flat or Phillips screwdriver, or even thumbscrews may be used.

The fragment pin holders 124 should have sufficient length to adequately support the fragment pins 130. In the preferred embodiment, the length of the pin holder 124 (and the length of the fragment pin through hole 132) is over ½ inch. The preferred surgical technique includes setting the fragment pins 130 through the fragment with the tip of the fragment pin 130 extending into the healthy, intact radius 28. For the example depicted in FIG. 2, two pins 130 are set beginning in the radial styloid and exiting on the opposite intact radial cortex, and a third pin 130 secures the dorsal fragment from dorsal and distal to volar and proximal, again exiting in the intact portion of the bone 28. Such pin placement allows the volar tilt of the wrist to be maintained. If necessary because of the condition of the radius 28, the pin holder 124 sufficiently supports the fragment pin 130 such that the tip of the fragment pin 130 may be driven merely into the fragment, with support sufficient to reduce the fragment being provided by the fragment pin holder 124 without cross-fracture attachment into the radius 28. The preferred fragment pins 130 are 0.062 inch diameter wires. The wires can be drilled free hand or using the pin holders 124 as templates.

In the preferred embodiment, one of the pin holders 124 includes two fragment pin through holes 132. The two holes 132 are separated by roughly ½ inch and extend parallel to each other, to support two fragment pins 130 in a generally parallel spaced relationship. The second pin holder 124 includes a single fragment pin through hole 132.

One of the important advantages of the preferred embodiment is the flexibility it provides the surgeon in the surgical technique used. After the wrist is immobilized with the distractor device 12, the surgeon may determine where to place fragment pins 130 and how many fragment pins 130 should be used. Wire placement can be varied depending on fracture configuration and/or surgeon's preference. The fragment pins 130 may be driven into the bone fragments either threaded through the pin holder 124 or even before the fragment pin supports 24 are placed into the outrigger track 98. After the fragment pins 130 are positioned by the surgeon, the various degrees of adjustment freedom can each be tightened to secure the position of the fragments relative to the outrigger 22, and via the main body 16 relative to the radius 28.

Further, movement of the wrist joint during healing is an important part of the healing process. The present invention contemplates fixation of the fragment pins 130 even after the distal body 18 is removed from the second metacarpal 40. That is, one preferred surgical technique for the present invention involves two separate healing durations. In the first healing duration, the fixator 10 is secured to the distal radius 28, to the second metacarpal 40, and to the bone fragments. Once the bone fragments begin to heal, some stress on the joint is beneficial to promote additional healing and faster bone growth. After an initial healing duration when the surgeon is confident that fracture stability exists, a wrist-release surgery is performed, in which the metacarpal pins 30 are removed from the metacarpal 40 and the distal body 18 is removed from the main body 16. After the wrist release surgery, the patient can attain at least a limited degree of wrist flexation, which improves the secondary healing. The fragment pins 130 still hold the fragments in place to ensure that the wrist is not refractured during this secondary healing. After a secondary healing duration, a third surgery is performed to fully remove the external fixator 10.

Another important advantage of the preferred embodiment is the range of materials which can be used. The preferred embodiment is designed to handle stresses of the Colles' fracture fixation by using a plastic material. The plastic material used is significantly lighter than metals traditionally used for fixators. The plastic material used, together with the sizes and shapes discussed herein, allows the fixator 10 to be sufficiently rigid without permitting the degree of bending which is inherently possible in most metal fixation structures. The preferred material for the preferred embodiment is a high density plastic, partially glass filled. Because this plastic material is not sufficiently strong to penetrate bone (and for FDA approval reasons), traditional metal bone pins 30 are used, but the remaining parts can all be molded of plastic. In particular, the main body 16, the distal body 18, the secureable adjustment segment 20, the slide plate 78, the outrigger 22 and the fragment pin supports 24 are all formed of plastic. As a moldable material, manufacture of the fixator 10 can be made less expensive. If desired for cost or thread strength reasons, the set screws 36, 44, 54, 70, 86, 88, 122, 134 and bolts 58, 60, 104, 116, 128 described herein may be formed as traditional metal structures as well. The preferred material is an ULTEM 1000, 20% glass bead filled plastic, which is an engineered high density poly-ether-imide (PEI) plastic suitable for orthopaedic devices and available from GE Plastics. Other suitable plastic materials might include poly-phenyl-sul-fone (PPSU) (e.g. Amoco Radel R), polysulfone (PSU) (e.g. Amoco Udel P), polyaryletherketone (PAEK) (e.g. BASF Ultrapek), liquid crystal polymer (LCP) (e.g. Vectra); and polyketone (e.g. Amoco Kadel E).

Although the present invention has been described with reference to preferred embodiments, workers skilled in the art will recognize that changes may be made in form and detail without departing from the spirit and scope of the invention. As one example, while the preferred embodiment has been described as having a "main" body and a "distal" body, for certain applications it maybe desired to heal the joint by having the outrigger 22 supported by the bones distal of the fracture. In the case of a Colles' fracture, this would include attaching the main body 16 to the second metacarpal 40 and attaching the "distal" body to the radius 28. The relative dimension and sizes of the "main" body and the "distal" body would be adjusted accordingly. Thus a worker skilled in the art will appreciate that the term "distal" is used as a matter of convenience and does not necessarily indicate the orientation of the fixator 10 with respect to the fracture. Similarly, the term "horizontal" has been used as a reference direction associated with a generally horizontal, palm down orientation of the patient's arm/hand, i.e., with the radius and the ulna both at the same height and horizontal. Workers skilled in the art will appreciate that this reference direction will change when the orientation of the patient's hand or arm changes. As another example, while the preferred embodiment is intended for Colles' fractures, the invention could be in many respects equivalently applied to fractures of other long bones, such as the proximal radius, and either proximal or distal ends of the ulna, tibia, fibula, humerus, or femur.

What is claimed is:

1. An external fixator for a bone fracture in or adjacent a long bone, the external fixator comprising:

a main body adapted for external fixation to the long bone, the main body extending along a longitudinal axis generally parallel to a longitudinal axis of the long bone, the longitudinal axis of the long bone and the longitudinal axis of the main body together defining a reference plane;

an outrigger connected to the main body for extending over the bone fracture and generally perpendicular to the longitudinal axis of the main body, the outrigger extending from a proximal end connected to the main body to a distal end, such that the outrigger cantilevers over the bone fracture when the main body is fixed to the long bone;

a first bone fastener support adjustably attachable to the outrigger for adjustable movement along the outrigger in a first bone fastener support movement direction, the outrigger being formed such that the first bone fastener support movement direction is sloped at a non-perpendicular angle relative to the reference plane, such that movement of the first bone fastener support in the first bone fastener support movement direction changes the elevation of the first bone fastener support relative to the reference plane and the bone fracture; and a first bone fastener supported by the first bone fastener support for attachment into a bone fragment to fix the bone fragment relative to the long bone for a healing duration.

2. The external fixator of claim 1, wherein the first bone fastener support is slidably attached to the outrigger.

3. The external fixator of claim 2, wherein the outrigger defines a track for the first bone fastener support extending over the reference plane for movement of the first bone fastener support over the bone fracture, and the first bone fastener support slidably rides in the track.

4. The external fixator of claim 3, wherein the track has a first opening for introduction and removal of the first bone fastener support while the outrigger is connected to the main body, the first opening being located proximally on the outrigger toward the main body.

5. The external fixator of claim 4, wherein the track has a second opening for introduction and removal of a bone fastener support while the outrigger is connected to the main body, the second opening being located distally on the outrigger away from the main body.

6. The external fixator of claim 1, further comprising:

a second bone fastener support adjustably attachable to the outrigger for adjustable movement along the outrigger in a second bone fastener support movement direction, the second bone fastener support movement direction being non-perpendicular to the reference plane, the second bone fastener support movement direction being at a wrap around angle relative to the first bone fastener support movement direction.

7. The external fixator of claim 1, wherein the first bone fastener support movement direction, is at an angle of from 98° to 115° relative to the longitudinal axis of the main body.

8. The external fixator of claim 1, wherein the main body and the outrigger are formed of plastic.

9. The external fixator of claim 1, wherein the main body is adapted for external fixation to a radius, with the outrigger connected to the main body for extending over the wrist joint between the radius and a metacarpal for treatment of a Colles' fracture.

10. The external fixator of claim 1, wherein the main body extends distally, wherein the outrigger is secureable to the main body at a first position wherein the outrigger extends over the reference plane to the right of the main body when viewed in the distal direction and a second position wherein the outrigger extends over the reference plane to the left of the main body when viewed in the distal direction.

11. The external fixator of claim 1, wherein the outrigger comprises a first section for use in holding the bone fastener support such that the bone fastener support extends distally when the outrigger extends to the right of the main body and a second section for use in holding the bone fastener support such that the bone fastener support extends distally when the outrigger extends to the left of the main body.

12. The external fixator of claim 11, wherein the first section and the second section each comprise a track, the tracks joining at a common end point extended away from the main body.

13. An external fixator for a bone fracture in or adjacent a long bone, the external fixator comprising:

a main body adapted for external fixation to the long bone, the main body extending along a longitudinal axis generally parallel to a longitudinal axis of the long bone, the longitudinal axis of the long bone and the longitudinal axis of the main body together defining a reference plane;

an outrigger connected to the main body for extending over the fracture and generally perpendicular to the longitudinal axis of the main body;

a first bone fastener support adjustably attachable to the outrigger for adjustable movement along the outrigger in a first bone fastener support movement direction which is generally linear and non-perpendicular to the reference plane; and a second bone fastener support adjustably attachable to the outrigger for adjustable movement along the outrigger in a second bone fastener support movement direction which is generally linear and non-perpendicular to the reference plane, the second bone fastener support movement direction being at a wrap around angle relative to the first bone fastener support movement direction.

14. The external fixator of claim 13, wherein the wrap around angle is greater than 15°.

15. The external fixator of claim 13, wherein the outrigger defines a first track portion for the first bone fastener support and a second track portion for the second bone fastener support, and wherein the first track portion and the second track portion are separated at the wrap around angle in the outrigger by a strengthening web.

16. An external fixator for a bone fracture immediately in or adjacent a long bone adjacent a joint between a long bone and a second bone, the external fixator comprising:

a main body adapted for external fixation to the long bone, the main body extending along a longitudinal axis generally parallel to a longitudinal axis of the long bone, the longitudinal axis of the long bone and the longitudinal axis of the main body together defining a reference plane;

an outrigger connected to the main body for extending over the fracture and generally perpendicular to the longitudinal axis of the main body;

a first bone fastener support adjustably attachable to the outrigger for adjustable movement in a first bone fastener support movement direction, wherein the outrigger is pivotably attached to the main body via a hinged connection providing a pivot axis generally parallel to the longitudinal axis of the main body such that pivotal adjustment of the outrigger changes an angle of the first bone fastener support movement direction relative to the reference plane.

17. The external fixator of claim 16, wherein the outrigger is pivotably attached to the main body such that the first bone fastener support movement direction can be selected at positive and negative angles relative to the reference plane.

18. The external fixator of claim 16, wherein the outrigger is pivotably attached to the main body such that the first bone fastener support movement direction can be selected at a greater range of positive angles than negative angles.

19. An external fixator for a bone fracture in or adjacent a long bone, the external fixator comprising:

a main body adapted for external fixation to the long bone, the main body extending along a longitudinal axis generally parallel to a longitudinal axis of the long bone, the longitudinal axis of the long bone and the longitudinal axis of the main body together defining a reference plane;

an outrigger connected to the main body for extending over the fracture and generally perpendicular to the longitudinal axis of the main body, the outrigger having a proximal end near the main body and a distal end away from the main body;

a first bone fastener support adjustably attachable to the outrigger for adjustable movement proximally and distally along the outrigger, the first bone fastener support being received at the proximal end of the outrigger; and a second bone fastener support adjustably attachable to the outrigger for adjustable movement proximally and distally along the outrigger, the second bone fastener support being received at the distal end of the outrigger, such that the first bone fastener support can be removed from or attached to the outrigger through the proximal end of the outrigger without removing the outrigger from the main body and without removing the second bone fastener support from the outrigger, and such that the second bone fastener support can be removed from or attached to the outrigger through the distal end of the outrigger without removing the outrigger from the main body and without removing the first bone fastener support from the outrigger.

20. An external fixator for a bone fracture in or adjacent a long bone, the external fixator comprising:

a main body adapted for external fixation to the long bone, the main body having a longitudinal axis running generally parallel to a longitudinal axis of the long bone, the longitudinal axis of the long bone and the longitudinal axis of the main body together defining a reference plane;

an outrigger attachable to the main body for extending over the fracture and generally transverse to the longitudinal axis of the main body, the outrigger when attached to the main body being adjustable in a first adjustment direction which allows changing of elevation of the outrigger relative to the reference plane, the outrigger comprising:
  a first slide portion extending at a first slide angle relative to the first adjustment direction; and
  a second slide portion extending at a second slide angle relative to the first adjustment direction;

a first bone fastener support adjustably attachable to the outrigger via the first slide portion for adjustable movement along the outrigger; and a second bone fastener support adjustably attachable to the outrigger via the second slide portion for adjustable movement along the outrigger, wherein the second slide portion is angled relative to the first slide portion allowing adjustable changes to elevation of at least one of the bone fastener supports relative to the reference plane without moving the outrigger relative to the main body.

21. The external fixator of claim 20, wherein the first slide portion is disposed proximally and the second slide portion is disposed distally on the outrigger relative to the main body, and wherein the second slide portion is angled relative to the reference plane.

* * * * *